United States Patent
Fisher et al.

(10) Patent No.: US 7,382,125 B2
(45) Date of Patent: Jun. 3, 2008

(54) TUNED FREQUENCY PORTAL FOR POWER TRANSFER IN MRI ENVIRONMENT

(75) Inventors: Stephen Douglas Fisher, Winter Springs, FL (US); Robert Andrew Harwell, Orlando, FL (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 442 days.

(21) Appl. No.: 11/224,252

(22) Filed: Sep. 12, 2005

(65) Prior Publication Data

US 2007/0073140 A1 Mar. 29, 2007

(51) Int. Cl.
*G01V 3/00* (2006.01)
(52) U.S. Cl. ........................ 324/307; 324/300
(58) Field of Classification Search ........ 324/300–322; 600/407–455; 128/920, 922
See application file for complete search history.

(56) References Cited

U.S. PATENT DOCUMENTS

| | | | | |
|---|---|---|---|---|
| 4,628,264 A * | 12/1986 | Rzedzian | ..................... | 324/322 |
| 4,737,712 A | 4/1988 | Stormont et al. | | |
| 5,200,703 A * | 4/1993 | Popp et al. | ................. | 324/322 |
| 5,733,247 A * | 3/1998 | Fallon | ......................... | 600/410 |
| 6,585,660 B2 * | 7/2003 | Dorando et al. | ............ | 600/486 |
| 6,663,570 B2 * | 12/2003 | Mott et al. | ................... | 600/486 |
| 6,711,434 B2 * | 3/2004 | Kramer et al. | ............. | 600/509 |
| 7,123,015 B2 * | 10/2006 | Koste et al. | ................ | 324/322 |
| 7,221,159 B2 * | 5/2007 | Griffiths et al. | ............. | 324/318 |
| 2008/0004904 A1 * | 1/2008 | Tran | .............................. | 705/2 |

* cited by examiner

*Primary Examiner*—Brij Shrivastav

(57) ABSTRACT

A circuit for isolating line voltage from a patient in an MRI environment, uses a filter network tuned to line voltage and incorporating blocking capacitors to eliminate the need for bulky air core transformers, complex energy transfer systems, and ferromagnetic components, while providing reduced heating such as might produce patient discomfort.

26 Claims, 1 Drawing Sheet

TUNED FREQUENCY PORTAL FOR POWER TRANSFER IN MRI ENVIRONMENT

CROSS-REFERENCE TO RELATED APPLICATIONS

STATEMENT REGARDING FEDERALLY SPONSORED RESEARCH OR DEVELOPMENT

BACKGROUND OF THE INVENTION

The present invention relates generally to magnetic resonance imaging (MRI) equipment and in particular to a method of providing electrically isolated power to patient monitoring equipment used in conjunction with MRI.

Magnetic resonance imaging can provide sophisticated images of the human body by detecting faint nuclear magnetic resonance (NMR) signals primarily from concentrations of hydrogen protons. In MRI, the patient is located in a strong polarizing magnetic field and hydrogen protons of the patient's tissues are excited into precession with a strong radio frequency (RF) pulse. A series of applied gradient magnetic fields are switched on and off to spatially encode the protons by phase and frequency after which sensitive antennas are used to detect the NMR signals which can then be reconstructed into images.

The MRI machine is a difficult environment for other electrical instrumentation. The switched magnetic gradients and the RF pulse create electromagnetic interference and the MRI receiving antenna is sensitive to interference from other devices. Magnetic materials such as those used in transformer and inductor cores must be eliminated from the region of the MRI machine because of the extremely strong polarizing magnetic field.

Often it is necessary to monitor physiological data of the patient in the MRI room before or during scanning. Such monitoring equipment may, for example, include blood pressure meters, anesthetic gas monitors, oximeters and ECG amplifiers requiring a source of electrical power.

If line power is used to power such monitoring equipment, care must be taken to isolate patient contacting portions of the equipment from the source of the line power, typically, 120 to 240 volts and 20 amperes or more. Conventional iron-core transformers can provide such isolation, but are impractical in the MRI environment because of their ferromagnetic cores. Ferrites, in contrast, can become saturated in the magnetic field of the MRI magnet, often 0.5 Tesla or more. Air core transformers, such as provide adjacent windings of copper conductors without a ferromagnetic core, may be used; however, air core transformers are bulky and inefficient, and this latter drawback generates heat that can be a problem in a patient contacting device.

U.S. Pat. No. 4,737,712 describes a method of providing isolated power to a patient contacting instrument by converting electrical power into another form (e.g. optical, mechanical, or acoustic power) and then reconverting those alternative forms of the electrical energy back into electrical energy for use by the device. The conversion process provides inherent limitations in power transfer. This approach requires complex mechanisms and is practically limited to extremely low power transfer.

BRIEF SUMMARY OF THE INVENTION

The present inventors have recognized that power can be effectively transferred and isolated in an MRI environment by the dielectric of high voltage but small capacitance capacitors forming part of a tuned circuit blocking the normal frequency (60 Hertz) of line current. This simple approach does not require complex conversions from one type of power to another and uses a low cost circuit design. The transferred power is shifted in frequency to avoid the blocking effect of the tuned circuit.

Unlike an air core transformer approach, the present invention produces very little radiated electrical power such as may interfere with the MM machine and the circuit may be compact. Isolation is provided in two directions limiting power to the patient and limiting power to the equipment.

Specifically, the present invention provides an MRI compatible patient monitor having a patient sensor circuit communicating with the patient and including an electrical load. The invention provides an alternating current power source attached to a source of line power and having a frequency different from a line frequency and an electrical filter connecting the alternating current power source to the electrical load. The electrical filter has a rejection band encompassing the line frequency.

It is thus is one object of at least one embodiment of the invention to provide a simple isolating circuit compatible with the environment of an MRI machine, and that prevents line voltage faults from being communicated to patient contacting portions of a patient sensor.

The electrical filter may provide isolating capacitors between the alternating current power source and the patient sensor circuit.

It is thus another object of at least one embodiment of the invention to block all flow of direct current.

The total capacitance between the alternating power source and the load may be less than 1000 picofarads.

It is thus another object of at least one embodiment of the invention to provide a high impedance limiting all low frequency current flow.

The electrical filter may be a series resonant inductance and capacitance.

It is thus one object of at least one embodiment of the invention to provide a passive filter blocking line current frequencies without significant heating.

The alternating current power source may provide a power and return conductor and the electrical filter may provide a capacitor in series with each of the power and return.

It is thus another object to the invention to prevent dangerous current flows on a return conductor.

Each capacitor may have a breakdown voltage of no less than one thousand volts.

It is thus another object of at least one embodiment of the invention to prevent the flow of current at extremely high voltages, for example, that may be associated with other medical equipment.

The alternating current power source may provide a first phase of alternating current on a power conductor and an opposite phase of alternating current on a return conductor.

It is thus another object of at least one embodiment of the invention to provide extremely low radio emissions from the power and return conductor by providing balanced current flows whose fields cancel each other out.

Each power conductor and return conductor may provide a series resonant, series connected, inductor and capacitor or may use a simple resistance-capacitor circuit.

It is thus another object of at least one embodiment of the invention to provide balance in the filter circuitry among the power and return conductors to reduce electromagnetic interference and to ensure that neither the power nor return conductor can conduct fault currents.

The circuit may include a resistance in series with the series connected inductor and capacitor.

It is thus one object of at least one embodiment of the invention to provide a range of blocked frequencies to accommodate variations about normal line frequency.

The circuit may further include a parallel-connected inductor and capacitor bridging the power and return lines.

It is thus another object of at least one embodiment of the invention to reduce high frequency harmonics of the line frequency such as those created by the non-linear loads of rectifier diodes and thereby reduce radio emissions.

The alternating current power source may have a frequency at least 100 times the line frequency.

Thus it an object of at least one embodiment of the invention to shift the frequency of the source of power away from the line frequency to prevent attenuation of the transmitted power by the electronic filter.

The alternating current power supply may have a frequency of at least 10 kilohertz.

It is another object of at least one embodiment of the invention to provide a high frequency alternating current power source allowing adequate power transfer across small isolating capacitors.

The patient sensor may measure any physiological parameter, including for example, a blood pressure, temperature, respiration, specific blood oxygen, or ECG.

Thus it is another object of at least one embodiment of the invention to provide an isolating system generally useful for a wide variety of patient monitoring apparatus.

The electronic filter may have an impedance of greater than five mega-ohms at the line frequency.

It is thus another object of at least one embodiment of the invention to provide predetermined limits on the amount of current flow that may occur in a direct fault situation.

These particular objects and advantages may apply to only some embodiments falling within the claims and thus do not define the scope of the invention.

DETAILED DESCRIPTION OF THE PREFERRED EMBODIMENT

Figure 1:
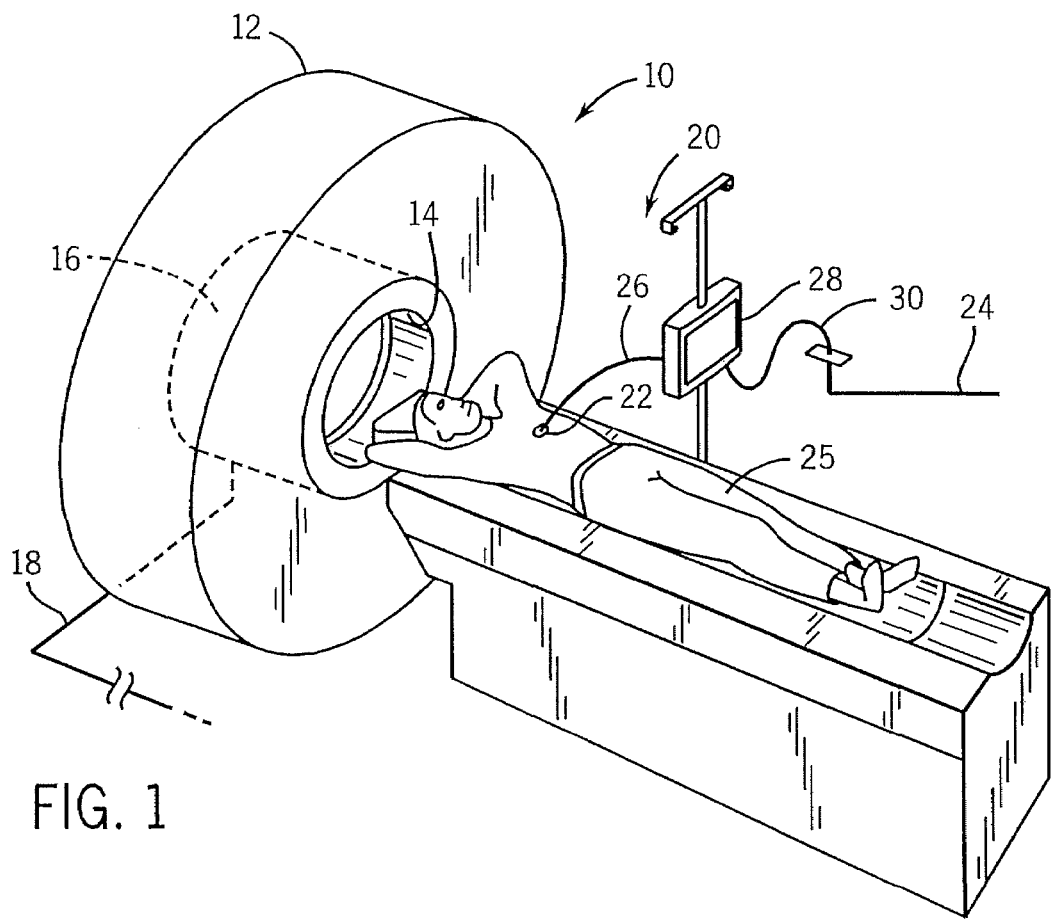
FIG. 1 is a simplified perspective view of an MRI machine including an MRI coil assembly for transmitting and receiving radio frequency electronic signals and showing positioning of a patient prior to a scan, the patient having an on-patient sensor unit provided with power from a monitoring unit connected to line power.

Referring now to FIG. 1, an MRI machine 10 may include a polarizing magnet 12, for example, that creates a strong polarizing magnetic field. The polarizing magnetic field is such as to saturate ferrites and prevent the use of ferromagnetic materials in the region of the MRI machine 10.

The polarizing magnet 12 may include a bore 14 into which the patient 25 may be placed for scanning. Within the bore 14, the patient 25 is surrounded by a coil set 16 providing for an RF excitation pulse, one or more gradient magnetic fields, and an antenna for detecting a faint NMR signal, as will be understood to those of ordinary skill in the art. The coil set 16 communicates with remote analysis signal processing electronics and computers (not shown) via cables 18.

The present invention provides a patient monitoring system 20 having an on-patient sensor unit 22 requiring a source of electrical power. The on-patient sensor unit 22 may, for example, include transducers for detecting blood pressure, amplifiers for ECG signals; light emitting diode/photodetector pairs for specific blood oxygen measurement and the like. The general construction of such sensor units are well know in the art.

The on-patient sensor unit 22 communicates via lead 26 to a patient monitoring system 20. The lead 26 is sized to allow the patient 25 to be moved into the bore 14 for scanning and ideally for the patient monitoring system 20 to operate during that scanning process.

The patient monitoring system 20 in turn may receive a source of line power 24 through a conventional power cord 30 plugging into a floor mounted outlet or the like. The on-patient sensor unit 22 must be electrically isolated from line power 24, in the event of an unexpected fault condition that results in the breakdown of blocking elements or insulation normally between the patient 25 and line power 24.

Figure 2:
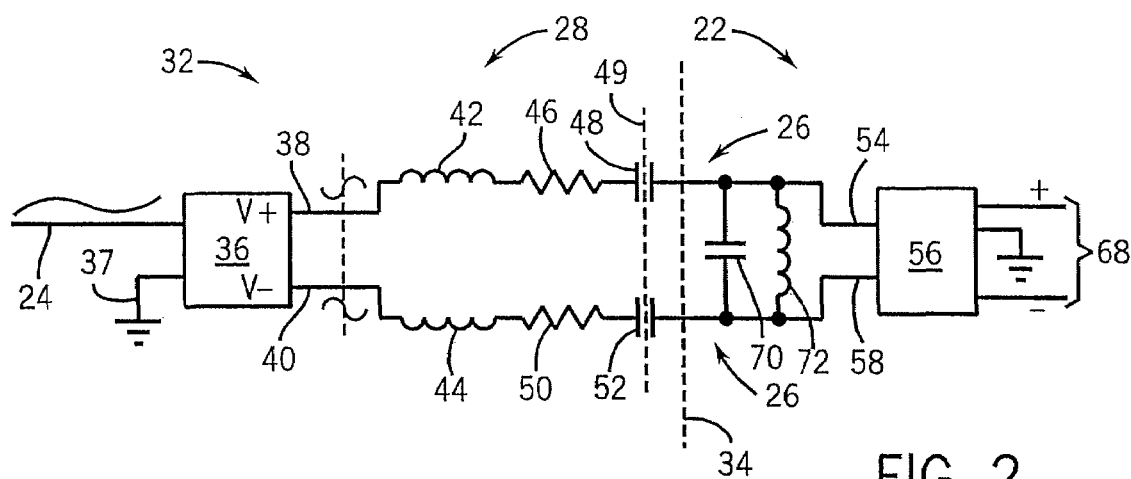
FIG. 2 is a schematic of the isolation circuit of the present invention as positioned in the monitoring unit or the on-patient sensor unit of FIG. 1 showing the conversion of line power to balanced high frequency alternating current (AC) waveforms passing through a filter to be used by patient contacting sensors.

Referring to FIG. 2, the present invention provides an isolating circuit 32 positioned between the patient 25 and line power 24 preventing the flow of line power 24 to the patient 25 in the event of a fault condition. It will be understood, that the isolating circuit 32 may be placed anywhere between line power 24 and on-patient sensor unit 22, and thus can be positioned in the on-patient sensor unit 22 or in the monitoring unit 28 or prior to monitoring unit 28 in the power cord 30. For the purposes of clarity and discussion, it will be assumed that the isolating circuit 32 will be placed in part in on-patient sensor unit 22 and in part in monitoring unit 28 as indicated by a dividing line 34.

To the left of dividing line 34, the isolating circuit 32 provides an alternating current power source 36 receiving a source of line power 24 typically being 120 volts at 60 hertz referenced with respect to a ground lead 37. The alternating current power source 36 converts the line power 24 into two out-of-phase, equal amplitude, waveforms, one at a V+ output 38 and the second at a V− output 40. In the preferred embodiment, the waveform at V+ output 38 is a sine wave of frequency of no less than ten kilohertz and preferably thirty megahertz with approximately 20 volts amplitude and the V− output 40 is exactly 180 degrees out of phase with the V+ output 38, but identical in frequency and amplitude.

The alternating current power source 36 may employ a rectifier, such as a full wave rectifier, followed by a filter to convert the line power 24 into a DC voltage. The necessary waveforms may then be synthesized from the DC voltage according to methods well known in the art, for example, using a switching amplifier driven by a stable reference oscillator source.

Referring still to FIG. 2, each of V+ output 38 and V− output 40 connect to one end of an inductor 42 and 44, respectively. Inductor 42 is connected in series with resistor 46 and capacitor 48, whereas inductor 44 is connected in series with resistor 50 and capacitor 52.

The capacitors 48 and 52 block all direct current flow past a dielectric barrier 49 produced by the insulating separators between the capacitor plates. In the preferred embodiment, the capacitors 48 and 52 are approximately 50 picofarads and have a breakdown voltage of at least 1000 volts and preferably 2.5 kilovolts to produce a leakage current of less than fifty microamperes at 60 hertz for a worst case line voltage fault. Generally the total capacitance between the alternating power source and the load is limited to be less than 1000 picofarads and preferably less than 100 picofarads and the total impedance between the alternating power source and the load is greater than five mega-ohms and preferably greater than 50 mega-ohms.

Figure 3:
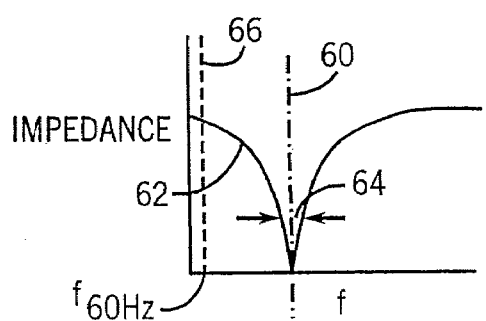
FIG. 3 is a plot of the impedance of the filter of FIG. 2 showing the frequency of the AC power source and line frequency.

The remaining terminal of capacitor 48 connects to a first input 54 of an AC to DC converter 56, whereas the remaining terminal of capacitor 52 connects to a second input 58 of the AC to DC converter 56. The AC to DC converter 56 may, for example, be a half wave or full wave rectifier or other rectification system known in the art followed by filter elements such as capacitors or inductors to provide an output of plus and minus DC voltage 68 referenced to a ground, for example, through the use of a divider. Referring also to FIG. 3, the value of each of inductors 42 and 44 and capacitors 48 and 52 are selected to provide a series resonance at a frequency 60 of the alternating current power source 36 being in the preferred embodiment thirty megahertz. The series resonance creates a pass band 64 around thirty megahertz where power transmitted through the isolating circuit 32 is maximized. The resistors 46 and 50 control the width of a rejection band 64 ensuring that slight deviations in frequency 60 of the alternating current power source 36 are passed by the resulting series resonant circuit.

Because the frequency of resonance (and thus the center of the pass band 64) is proportional to a ratio of the values of the inductors 42 and 44 and the capacitors 48 and 52, each of the series resonance circuits of inductor 42, and capacitor 48 and of inductor 44 and capacitor 52 are together and individually tuned to the same frequency.

The frequency 66 of the line power 24 is substantially lower than the frequency of the alternating current power source 36, in the preferred embodiment, more than 100 times lower, thus ensuring that there is relatively little attenuation of the power generated by the alternating current power source 36 as received by the AC to DC converter 56.

The nonlinear characteristics of the diodes of the AC to DC converter 56 may create a varying load such as may induce asymmetric currents and high frequency harmonics in the leads 26 generally passing between capacitors 48 and 52 and inputs 54 and 58. Accordingly, a parallel resonance circuit formed of capacitor 70 and inductor 72 may be placed across inputs 54 and 58 and tuned to create a low impedance at possible frequencies of radio frequency harmonics. The exact tuning of these devices can be determined empirically by observing, for example, on a spectrum analyzer, the frequencies of electromagnetic interference. Alternative loads to the AC to DC converter 56 include resistive loads and electrical lamps such as LEDs.

The capacitors provide extremely lightweight isolation with low heating determined by the values of resistors 46 and 50. The circuit employs no ferromagnetic components.

As will be apparent from the above description, the present invention could alternatively employ an unbalanced approach in which the V− output 40 is simply a ground reference. Alternatively the V+ output 38 and V− output 40 may be out of phase square waves or other waveforms with the possible disadvantage of increased electromagnetic interference. Further, it will be recognized that a simple series resistor-capacitor circuit, providing, for example, a high pass filter allowing passage of the high frequency of the alternating current power source 36 but blocking the lower frequency of the line power 24 can be used. Other well-known passive filter designs can also be used.

It is specifically intended that the present invention not be limited to the embodiments and illustrations contained herein, but include modified forms of those embodiments including portions of the embodiments and combinations of elements of different embodiments as come within the scope of the following claims.

We claim:

1. An MRI compatible patient monitor, comprising:
a patient sensor circuit communicating with the patient and including an electrical load;
an alternating current power source attached to a source of line power and producing power at a frequency different from a line frequency of the line power; and
an electrical filter connecting the power produced by the alternating current power source to the electrical load, the electrical filter having a rejection band encompassing the line frequency;
wherein line voltage faults are not communicated between the patient sensor circuit and the alternating current power source.

2. The patient sensor circuit of claim 1 wherein the electrical filter provides isolating capacitors between the alternating current power source and the patient sensor circuit blocking direct current (DC) flow.

3. The patient sensor circuit of claim 2 wherein the capacitors are less than 1000 picofarads.

4. The patient sensor circuit of claim 2 wherein the electrical filter is a series resonant inductance and capacitance.

5. The patient sensor circuit of claim 2 wherein the electrical filter is a series resistance and capacitance.

6. The patient sensor circuit of claim 1 wherein the alternating current power source provides a power and return conductor and the electrical filter provides a capacitor in series with each of the power and return.

7. The patient sensor circuit of claim 6 wherein the capacitors have a breakdown voltage of no less than 1 kV.

8. The patient sensor circuit of claim 6 wherein the alternating current power source provides a first phase of alternating current on the power conductor and an opposite phase of alternating current on the return conductor.

9. The patient sensor circuit of claim 8 wherein each of the power conductor and return conductor provide series resonant, series connected inductors and capacitors.

10. The patient sensor circuit of claim 8 wherein each of the power conductor and return conductor provide a tuned series connected resistor and capacitor.

11. The patient sensor circuit of claim 8 further including a resistance in series with the series connected inductor and capacitor.

12. The patient sensor circuit of claim 8 further including a parallel-connected inductor and capacitor bridging the power and return lines of the electrical filter set to reduce emanated electrical interference.

13. The patient sensor circuit of claim 1 wherein the alternating current power source has a frequency at least 100 times the line frequency.

14. The patient sensor circuit of claim 1 wherein the alternating current power supply has a frequency of at least on 10 kHz.

15. The patient sensor circuit of claim 1 wherein the patient sensor circuit is a blood pressure measuring circuit.

16. The patient sensor circuit of claim 1 wherein the patient sensor is a monitoring circuit selected from the group consisting of temperature, respiration, specific blood oxygen, and ECG.

17. The patient sensor circuit of claim 1 wherein the electrical filter has an impedance of greater than five mega-ohms at the line frequency.

18. The patient sensor circuit of claim 1 wherein the load is a rectifier circuit.

19. The patient sensor circuit of claim 1 wherein the load is a resistance.

20. The patient sensor circuit of claim 1 wherein the load is an electrical light.

21. An MRI compatible patient monitor, comprising:
a patient sensor circuit communicating with the patient and including an electrical load;
an alternating current power source having a frequency different from a line frequency and providing a power and return conductor; and
an isolating circuit providing at least two isolating capacitors, one on each of the power and return conductors between the alternating current power source and the electrical load; and
wherein the isolating circuit provides a resistance to electrical flow at a line frequency of greater than 50 mega-ohms.

22. The patient sensor circuit of claim 21 wherein the capacitor has a breakdown voltage of no less than 2.5 kV.

23. The patient sensor circuit of claim 21 wherein the alternating current power source provides a first phase of alternating current on the power conductor and an opposite phase of alternating current on the return conductor.

24. The patient sensor circuit of claim 21 further including a parallel-connected inductor and capacitor bridging power and return lines of the electrical filter set to reduce EMI.

25. The patient sensor circuit of claim 24 wherein the patient sensor circuit is a blood pressure circuit.

26. The patient sensor circuit of claim 24 wherein the patient sensor circuit is a monitoring circuit selected from the group consisting of temperature, respiration, blood oxygen, ECG signal, and blood pressure.

* * * * *